United States Patent
Duesing et al.

(10) Patent No.: US 8,853,895 B2
(45) Date of Patent: Oct. 7, 2014

(54) ELECTRIC MOTOR ARRANGEMENT FOR USE IN A MEDICAL, IN PARTICULAR IN A DENTAL HANDPIECE AND DENTAL HANDPIECE PART

(75) Inventors: Josef Duesing, Leutkirch (DE); Alfons Mader, Isny (DE); Johann Stempfle, Pfaffenhofen (DE)

(73) Assignee: Kaltenbach & Voigt GmbH, Biberach (DE)

( * ) Notice: Subject to any disclaimer, the term of this patent is extended or adjusted under 35 U.S.C. 154(b) by 550 days.

(21) Appl. No.: 13/092,714

(22) Filed: Apr. 22, 2011

(65) Prior Publication Data

US 2011/0269101 A1 Nov. 3, 2011

(30) Foreign Application Priority Data

Apr. 27, 2010 (DE) .......................... 10 2010 028 245

(51) Int. Cl.
*H02K 7/14* (2006.01)
(52) U.S. Cl.
USPC .............................................. 310/50; 310/90
(58) Field of Classification Search
USPC ............... 310/50, 90, 400–401; 433/131, 136
See application file for complete search history.

(56) References Cited

U.S. PATENT DOCUMENTS

| 4,534,732 A | 8/1985 | Strohmaier |
| 5,482,413 A * | 1/1996 | Argaud ......................... 408/124 |
| 5,938,441 A * | 8/1999 | Brenner ........................ 433/132 |
| 6,132,213 A * | 10/2000 | Knorpp et al. ................ 433/131 |
| 6,425,761 B1 * | 7/2002 | Eibofner ....................... 433/131 |
| 7,611,315 B2 * | 11/2009 | Duesing ....................... 409/233 |
| 2010/0233651 A1 | 9/2010 | Kuhn et al. |

FOREIGN PATENT DOCUMENTS

DE 33 32 627 4/1985
DE 10 2007 048 340 4/2009

* cited by examiner

*Primary Examiner* — Thanh Lam
(74) *Attorney, Agent, or Firm* — Marshall, Gerstein & Borun, LLP

(57) ABSTRACT

The invention relates to an electric-motor arrangement for a medical, in particular dental, hand piece which has a motor housing (2) and a rotor (4) which is arranged in the motor housing (2) so that it can be rotated about an axis (L) via a first bearing (6) and a second bearing (8). A stator (14) is arranged around the rotor (4) in relation to the axis (L). The first bearing (6) is received in a first bearing flange (10), and the second bearing (8) is received in a second bearing flange (12). Both bearing flanges (10, 12) are composed of metal and adjoin the motor housing (2) directly by way of their circumferential faces (101, 121). As a result, running noise and vibrations can be reduced. Moreover, premature wear and/or failure can be prevented.

12 Claims, 12 Drawing Sheets

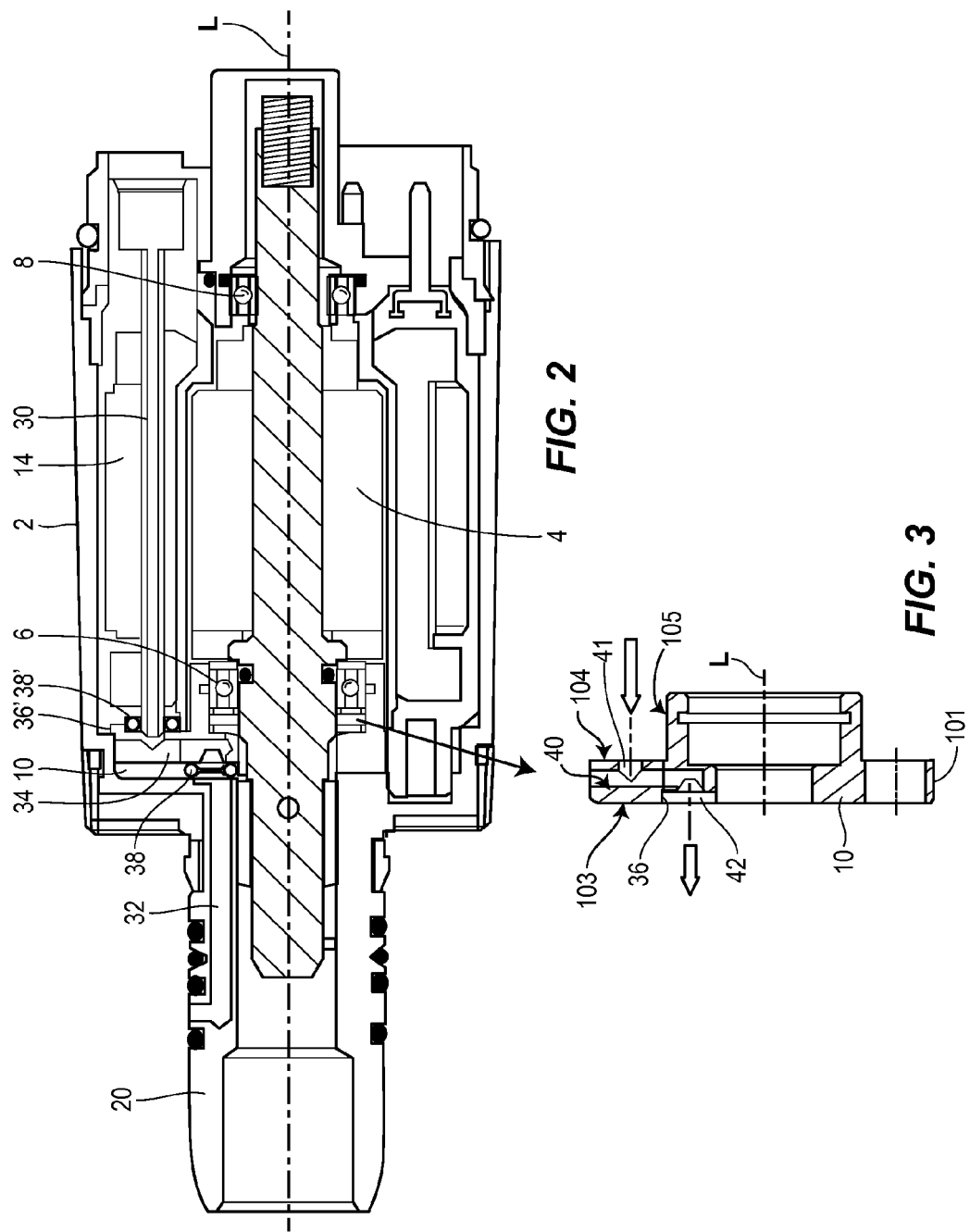

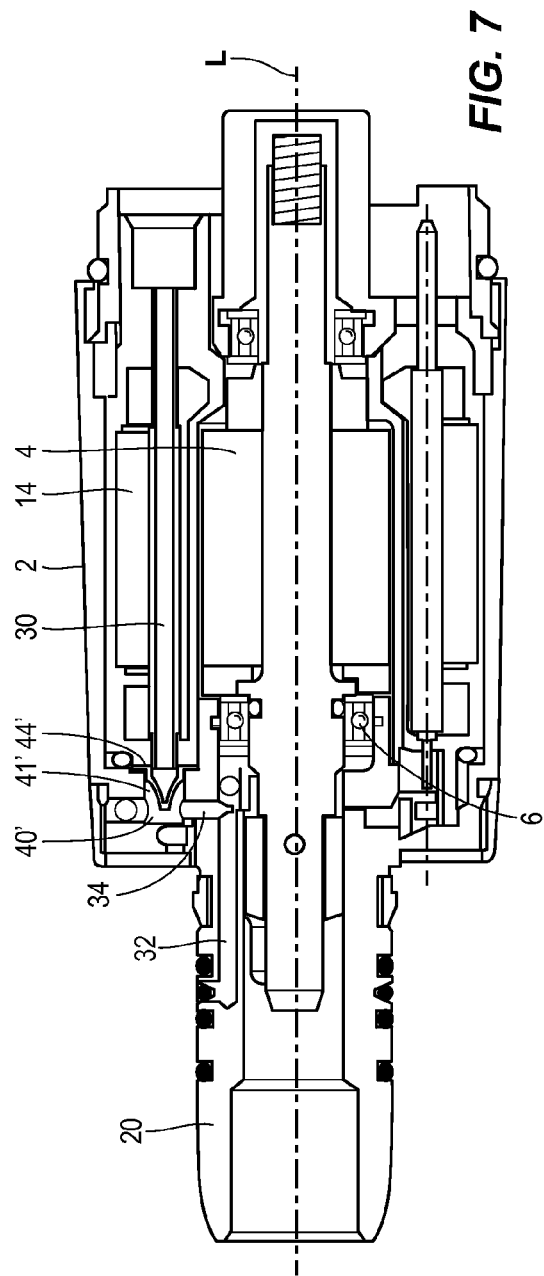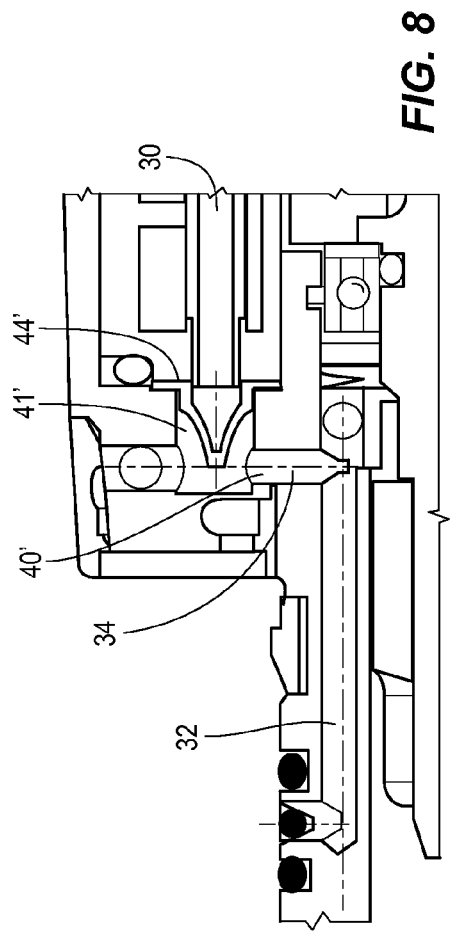

ELECTRIC MOTOR ARRANGEMENT FOR USE IN A MEDICAL, IN PARTICULAR IN A DENTAL HANDPIECE AND DENTAL HANDPIECE PART

BACKGROUND OF THE INVENTION

1. Field of the Invention

The present invention relates to an electric-motor arrangement for a medical, in particular dental, hand piece. The electric-motor arrangement comprises an electric motor, in particular a small dental motor, that is to say an electric motor of compact design which is provided, in particular, for use in dental hand-held units. An electric-motor arrangement of this type is also called "dental motor" or "small dental motor" for short in the following text.

2. Related Technology

In particular, the invention relates to an electric-motor arrangement which is provided for being connected via a coupling to a medical, in particular to a dental hand piece and angular piece, also called "hand piece" for short in the following text, the hand piece being configured for receiving a rotatably mounted tool and, if the electric-motor arrangement is coupled to the hand piece as provided, it being possible for a torque which is generated by the electric-motor arrangement to be transmitted to the tool. A corresponding arrangement is known, for example, from DE 33 32 627 A1. Furthermore, it can be provided, in particular, that a supply hose is connected via a further coupling so as to lie opposite the hand piece, in relation to the electric-motor arrangement, which supply hose serves to supply the electric-motor arrangement or the hand piece and has, for example, medium lines, by which media such as air and/or water can be transported in order to form a spray. A power line and/or a light cable can also be arranged in the supply hose.

In an electric-motor arrangement of this type, it is desirable that the rotor of the electric motor vibrates as little as possible in the operating state. A long service life of the electric motor is also desirable. Therefore, mounting of the rotor as exactly as possible is usually aimed for without any alignment errors, in particular in the case of a fast-running dental motor.

The prior art has disclosed a corresponding electric-motor arrangement which has a motor housing, in which a bearing point for the rotor is formed integrally on that side which points towards the hand piece coupling; on the opposite, that is to say "rear" side, a further, that is to say "rear" bearing flange is centered in the motor housing. DE 10 2007 048 340 A1 discloses a corresponding electric-motor arrangement, in which the bearing points are integrated directly into the stator body. The components for these known electric-motor arrangements are in part difficult to produce. Moreover, there is the risk of alignment errors with respect to the ideal motor axis, and the bearing seat can be deformed by thermal effects resulting from the motor coil and/or a sterilization, with the result that, furthermore, ball-bearing outer rings of the bearings are deformed and a bearing setting by springs fails. Both lead to an increase in running noise, vibrations and premature wear or failure.

The invention provides a corresponding electric-motor arrangement which vibrates less during operation and in the process has a longer service life.

According to the invention, an electric-motor arrangement is provided for a medical, in particular dental, hand piece which has a motor housing and a rotor which is arranged in the motor housing so that it can be rotated about an axis via a first bearing and a second bearing; moreover, the electric-motor arrangement has a stator which is arranged around the rotor in relation to the axis. Furthermore, the electric-motor arrangement has a first bearing flange, in which the first bearing is received, and a second bearing flange, in which the second bearing is received. The first bearing flange is composed of metal and has a first circumferential face which is arranged so as to adjoin the motor housing directly. The second bearing flange is composed of metal and has a second circumferential face which is likewise arranged so as to adjoin the motor housing directly.

Running noise and vibrations can be reduced as a result. Moreover, premature wear and/or failure can be prevented.

The stator is advantageously arranged clamped in between the first bearing flange and the second bearing flange and is preferably centered radially in the motor housing in relation to the axis by the first bearing flange and the second bearing flange. Negative influencing of a bearing point by distortion and/or diameter change of the stator as a consequence of heating of a winding of the stator and/or distortion as a result of sterilization are/is therefore prevented or at least considerably reduced. This results in a particularly short tolerance chain for the bearing prestressing which is defined substantially by the length of the stator along the axis and the spacing of contact shoulders for ball bearings on a shaft of the rotor.

Furthermore, the electric-motor arrangement advantageously has a coupling element, in particular in the form of a coupling pin, for connection of the electric-motor arrangement to the medical hand piece, the coupling element preferably being configured in one piece with the motor housing.

It is known to feed a medium, for example water or air, to the hand piece through a medium line; as a result, for example, a spray can be formed for cooling a processing location. In particular, the medium is provided for an attachment tool which can be driven by the electric motor and which is attached to the hand piece, for example a rotary tool. According to the prior art, the medium is fed first of all by the supply hose, subsequently by the electric-motor arrangement and finally in the hand piece. To this end, a first medium-line section of the medium line can be arranged in the electric-motor arrangement, which first medium-line section extends parallel to the rotational axis, or axis for short, of the motor. A small tubular piece is usually provided for this purpose, which is arranged laid in a groove in the shell of the motor housing, outside a magnetic yoke of the electric motor. In an electric-motor arrangement which has a coupling pin for connection to the hand piece, it is known, furthermore, that a second medium-line section extends through the coupling pin. The second medium-line section therefore usually extends radially further to the inside in relation to the rotational axis than the first medium-line section. Furthermore, a medium-diverting means therefore has to be provided which connects the first medium-line section to the second medium-line section so as to guide medium, and in the process overcomes the radial difference. It is known from the prior art to provide a curved pipe for this purpose, or a medium-diverting means which is formed by depressions in end faces of the motor housing and the coupling. It is a problem here that complicated sealing points result.

According to a second aspect, furthermore, the invention is based on the object of specifying a corresponding electric-motor arrangement which is improved with respect to the seal in the region of the medium-diverting means.

According to the second aspect of the invention, an electric-motor arrangement for a medical, in particular dental, hand piece is provided, which electric-motor arrangement has a motor housing, and a rotor which is arranged in the motor housing so that it can be rotated about an axis via a bearing, the bearing being arranged so that it is gripped in a bearing flange. Furthermore, the electric-motor arrangement has a stator which is arranged around the rotor in relation to the axis. Furthermore, the electric-motor arrangement has a coupling pin which is arranged around the axis, and a first medium-line section for guiding a medium, the first medium-line section extending radially outside the rotor in relation to the axis. Furthermore, the electric-motor arrangement has a second medium-line section for further guiding the medium, which second medium-line section extends in the coupling pin, the second medium-line section being arranged radially closer to the axis than the first medium-line section, and a medium-diverting means for a connection which guides the medium between the first medium-line section and the second medium-line section. Here, the medium-diverting means is formed in the bearing flange.

As a result, the seal in the region of the medium-diverting means can be simplified.

Furthermore, the electric-motor arrangement advantageously has a sealing seat for sealing between the first medium-line section and the medium-diverting means or between the medium-diverting means and the second medium-line section, the sealing seat being formed in the bearing flange and/or in the stator and/or in the coupling pin, and an O-ring preferably being arranged in the sealing seat.

The first medium-line section is preferably integrated into the stator.

It can also advantageously be provided that the electric-motor arrangement has a flat seal which bears against the bearing flange for sealing between the first medium-line section and the medium-diverting means or between the medium-diverting means and the second medium-line section.

The bearing flange preferably has a radial hole, by which a part of the medium-diverting means is formed.

Furthermore, it is known from the prior art to provide a suck-back stop in a medium line, which suck-back stop prevents the medium, that is to say, for example, water, being sucked back or flowing back from the hand piece into the electric-motor arrangement and/or into the supply hose. It is known here to form the suck-back stop as a lip valve which is arranged in the interior of the motor housing so as to be protected in the axial direction. There is the problem here that the extent of the electric-motor arrangement has to be of longer design in the direction of the rotational axis as a result. As an alternative, it is known to implement the suck-back stop so that an O-ring is arranged at an outlet hole of the coupling pin, which O-ring opens only when the supply pressure is applied. However, there is the risk here that this O-ring is damaged or moved out of its provided position by cleaning and/or plug-in operations for connection to the hand piece.

According to the invention, a hose element made from elastic material is preferably arranged in the radial hole in the bearing flange. As a result, a suck-back stop can be formed which is arranged so that it is protected and in the process saves space. The elastic material can be, for example, rubber, silicone or Viton. Here, the hose element is preferably arranged in such a way that it bears against the inner wall of the hole and, without the action of external forces, closes a feed hole for the medium from the stator. The hose element can bear against the inner wall as a result of the internal stress; in the case of pressure from the inflow side, the hose element can rise up from the inner wall and can allow the medium to flow through in the direction of the hand piece. In the pressure less state, the hose element correspondingly bears against the inner wall and closes the feed hole, with the result that the medium cannot flow back to the stator and/or to the supply hose.

Here, furthermore, the electric-motor arrangement preferably has a pin element which is arranged in such a way that it protrudes into the hose element and seals the latter radially to the outside with respect to the medium. As a result, it can be achieved, in particular, that the hose element can rise up from the inner wall only to a limited extent. Moreover, the pin element can close the hole in the radial direction towards the circumference of the bearing flange.

As an alternative to the above-described solution, a lip valve could also be arranged in the medium-diverting means. Furthermore, there is the possibility to form the bearing flange integrally into the housing.

Furthermore, the invention relates to a dental instrument part which has an outer surface which is composed of titanium. The dental instrument part can be, for example, an electric-motor arrangement, in particular an electric-motor arrangement as is shown further above.

It is known from the prior art to use metallic materials for housings and sleeves of dental instruments (hand pieces and angular pieces, turbines) and also dental motors, for example stainless steel, brass, aluminum or titanium. In order to achieve an attractive external appearance and a certain wear protection, the surfaces of the steel and brass parts are finished by chemical or galvanic coatings (NiCr) or PVD coating (PVD: physical vapor deposition), as a result of which there is also protection with respect to preparation processes such as disinfection and/or thermal disinfection and sterilization. It is a problem here that PVD coatings require a comparatively high outlay on apparatus and are expensive. Moreover, the layer thicknesses which can be achieved here are only a few micrometers. Furthermore, there is the risk that the layers flake off from the base material in the case of insufficient pre-treatment (for example, cleaning) and/or mechanical stress (for example, deformation). A further disadvantage of these housing parts made from steel/brass is their comparatively high weight.

Housings and sleeves made from aluminum can be produced inexpensively and have a comparatively low mass. In this case, the surfaces can also be protected against wear by hard anodic layers. However, the surfaces do not permanently withstand the media used during preparation.

Housings and sleeves made from titanium have a comparatively low mass. Without additional coating, titanium withstands an attack by media and processes, as are usually used in the context of preparation. In addition, they have excellent biocompatibility, with the result that, in particular, no allergic reactions are to be feared, that is to say, in particular, neither in a patient nor in a user. However, the wear protection is limited; in addition, impairments of the external appearance occur as a result of signs of use such as scratches.

Particularly high requirements with respect to the wear and scratch resistance are made of the surface of a coupling pin of dental couplings (for example, MULTIflex, INTRAmatic). Here, very accurate fits are required which are also not supposed to and/or must not change during operation as a result of the attachment of hard objects, that is to say, for example, hand pieces and angular pieces or turbines. The attachment of corresponding exchangeable instruments takes place very frequently in the dental practice. In order to avoid wear and "scoring" of these highly loaded components, they are produced from steel and are tempered. Here, ergonomic disadvantages which are produced as a result of the higher weight are accepted. Titanium and its alloys generally have poor tribological properties. This is manifested in comparatively high coefficients of friction, adhesive wear and a pronounced tendency to "scoring". Titanium and its alloys are therefore not used for coupling pins.

In dental instruments (hand pieces and angular pieces, turbines) and motors (pneumatic/electric motors), ergonomic aspects such as weight, but also robust and scratch-resistant surfaces with a satisfactory resistance to the media used during preparation (hot steam; alkaline and acidic cleaners; hydrocarbon compounds, inter alia) and processes (temperature, pressure, vacuum) and satisfactory haptics are decisive.

According to a further aspect, the invention is therefore based on the object of specifying a medical instrument part, in particular a dental instrument part, which is not damaged by preparation and in the process is improved ergonomically.

According to this aspect of the invention, a medical instrument part, in particular a dental instrument part, is provided which has an outer surface which is composed of titanium. The dental instrument part can be, for example, an electric-motor arrangement, as is shown further above. Here, the surface is tempered by a hardening process.

This achieves a situation where the medical instrument part can be configured with particularly low weight and can therefore be of ergonomically particularly advantageous design. Moreover, it is particularly scratch-resistant and abrasion-resistant and has a particularly low cold sweat tendency. Furthermore, the medical instrument part is particularly resistant to conventional preparation methods and processes such as thermal disinfection or hot-steam sterilization in autoclaves.

Here, the surface is advantageously tempered based on a thermo chemical diffusion process, the thermo chemical diffusion process preferably being what is known as "oxygen diffusion hardening."

The dental instrument part particularly preferably has a coupling pin which is provided for connection to a further dental instrument part, for example to a hand piece and angular piece, the outer surface being an outer surface of the coupling pin.

Dental instruments, in particular pneumatic/electric motors contain components which have to be maintained regularly and which have to be readily accessible for exchanging, for example in the case of a repair, such as a halogen lamp or an LED.

In order to avoid light scatter and in order to protect the electric contacts, halogen lamps and their connection plugs are arranged in the instrument so that they are protected by means of sleeves or protective caps or the like.

Here, it is known, for example, to fasten a sleeve to a motor housing by means of a threaded device. There is the problem here that thin, short threaded rings are deformed by comparatively low forces, as already have to be applied, for example, in order to overcome the thread friction, and therefore adhere all the more to the thread. It is only possible to release the threaded connection with a pressure which is distributed more or less uniformly over the entire circumference. Two fingers are usually used for the release, it being comparatively difficult to produce a correspondingly uniform pressure with two fingers. Furthermore, dirt can be deposited in the thread in practice by incorrect cleaning and care, which can lead to even considerably greater moments being required for the release. The "deformed sleeve and release problems" effect is therefore reinforced further.

Furthermore, it is known from the prior art that sleeves or protective caps are clipped on and are held via sprung pins/balls. In this case, the sleeves can also be pulled off in the case of moderate contamination. However, the ball/pin with cylinder spring design requires a relatively large amount of radial installation space, which opposes a compact overall embodiment. In the case of penetration of dirt, deposits and the like on account of insufficient care in the movement space of the ball, pulling the protective sleeve off is also made difficult in this solution.

Furthermore, it is known to clip on a sleeve or protective cap with an undercut, the sleeve being pressed or deformed for release. Although clipping a round sleeve onto an oval or flattened seat on the basic body is an elegant solution, above all, for thin, short sleeves and protective caps, this release of the sleeve is made difficult or prevented by deformation and adaptation to the oval shape of the basic body as a result of accumulation of contaminants or deposits in the movement space for the sleeve during release; Here, the undercut of the sleeve rises up out of the notch on the basic body.

The invention is therefore based, furthermore, on the object of specifying a dental instrument which has an improved holding mechanism for a sleeve or protective cap or the like.

According to this aspect of the invention, a dental instrument is provided which has a housing and an instrument part which is arranged removably on the housing. Here, the instrument part has an annular region which is arranged so as to reach around an outer circumferential face of the housing. A depression is arranged on the outer circumferential face, in which depression at least one preferably spherical, elastic holding part is received, an undercut being arranged in the annular region, into which undercut the elastic holding part engages.

In this way, a holding mechanism is provided which can be opened and closed easily and reliably, even in the case of relatively powerful pressing together with two fingers and under the influence of deposits and contaminants as a result of insufficient care in the gap between the instrument part and the housing. For example, the holding mechanism is suitable particularly satisfactorily for an instrument part in the form of a thin-walled sleeve or protective cap which is arranged, for example, on an electric-motor arrangement.

The depression is preferably configured in such a way that the elastic holding part only partially fills the volume which is defined by the depression. In this way, a "deformation space" is formed by the depression, which deformation space is available for deformation of the elastic holding part while the instrument part is being pulled off or attached.

BRIEF DESCRIPTION OF THE DRAWINGS

In the following text, the invention will be explained in greater detail using exemplary embodiments and in relation to the drawings, in which:

FIG. 2 shows a longitudinal section through an exemplary embodiment of an electric-motor arrangement according to the invention with a medium-diverting means, FIG. 3 shows the bearing flange shown in FIG. 2, in a separated state, FIG. 7 shows a further variation of the electric-motor arrangement shown in FIG. 2, with a suck-back stop, FIG. 8 shows an illustration of a detail from FIG. 7.

DETAILED DESCRIPTION

Figure 1:
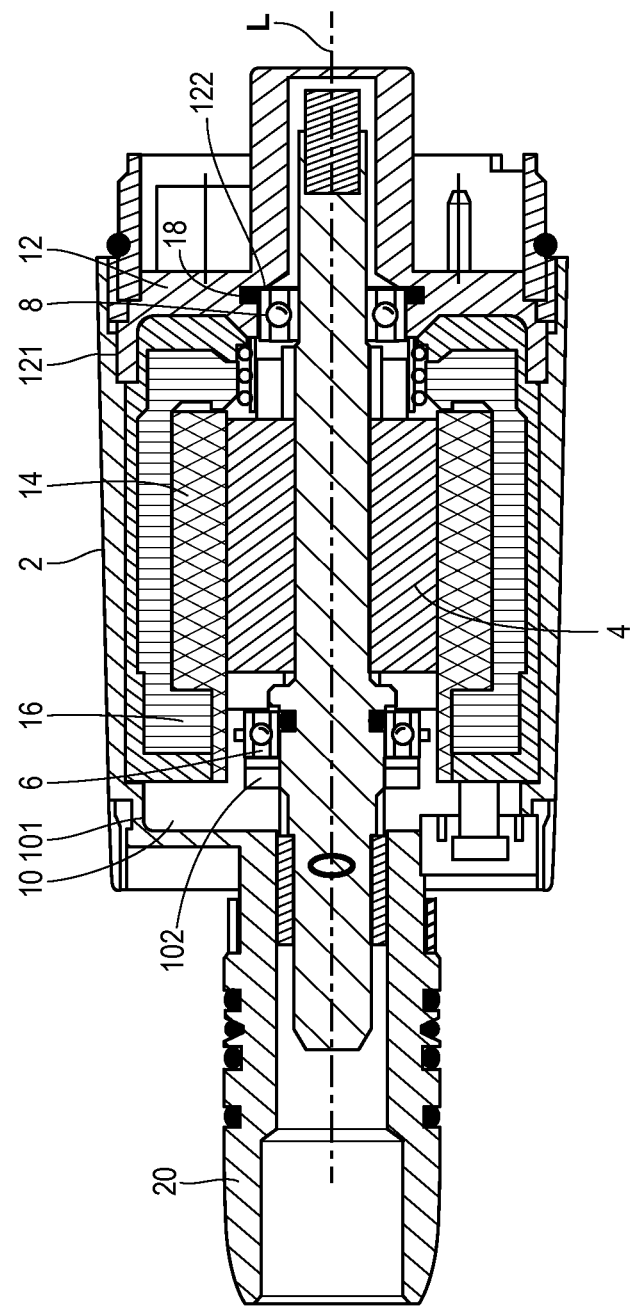
FIG. 1 shows a longitudinal section through an exemplary embodiment of an electric-motor arrangement according to the invention with metallic bearing flanges.

FIG. 1 shows a longitudinal section through a first exemplary embodiment of an electric-motor arrangement according to the invention. The electric-motor arrangement has a motor housing 2 and a rotor 4 which is arranged in the motor housing 2 so that it can be rotated about an axis L via a first bearing 6 and a second bearing 8. Moreover, the electric-motor arrangement has a stator 14 which is arranged around the rotor 4 in relation to the axis L. The stator 14 can contain plastic. Furthermore, the electric-motor arrangement has a first bearing flange 10, in which the first bearing 6 is received, and a second bearing flange 12, in which the second bearing 8 is received.

The first bearing flange 10 is composed of metal or is formed from metal, and has a first circumferential face 101 which is arranged so as to adjoin the motor housing 2 directly. In relation to the axis L, the first circumferential face 101 faces outwardly and adjoins an inwardly directed face of the motor housing 2. The second bearing flange 12 is likewise composed of metal or is formed from metal, and has a second circumferential face 121 which is arranged so as to adjoin the motor housing 2 directly. In relation to the axis L, the second circumferential face 121 faces outwardly and likewise adjoins a further or the inwardly directed face of the motor housing 2.

The first bearing 6 and the second bearing 8 can in each case be a ball bearing. The two bearings 6, 8 can in each case adjoin the respective bearing flange 10, 12 directly, that is to say can be gripped by the respective bearing flange 10, 12.

The motor housing 2 is preferably configured in one piece.

The stator 14 is advantageously arranged clamped in between the first bearing flange 10 and the second bearing flange 12. Here, the stator 14 advantageously adjoins the first bearing flange 10 directly on one side and adjoins the second bearing flange 12 likewise directly on the other side. Moreover, the stator 14 is preferably centered radially in the motor housing 2 in relation to the axis L by the first bearing flange 10 and the second bearing flange 12. A possible change in shape or size of the stator 14, for example as a result of thermal expansion, cannot have a direct effect on the two bearings 6, 8 as a result of this arrangement. The sensitivity of the electric-motor arrangement in the case of a sterilization is also reduced considerably as a result. Overall, this leads to fewer vibrations being produced during operation of the electric motor.

As is the case in the exemplary embodiment shown, the electric-motor arrangement can have, furthermore, a coupling element, in particular in the form of a coupling pin 20, to be precise for connecting the electric-motor arrangement to the medical or dental hand piece. Here, the coupling element or the coupling pin 20 is preferably configured in one piece with the motor housing 2. As a result, vibrations and running noise can be reduced even further.

As is apparent by way of example from FIG. 1, it can be provided, in particular, that the first bearing flange 10 and the second bearing flange 12 are in each case configured separately. Furthermore, the first bearing flange 10 can have a contact shoulder 102 for the first bearing 6, and the second bearing flange 12 can have a further contact shoulder 122, to be precise for contact with the second bearing 8.

A first O-ring 16 can be provided for sealing between the first bearing 6 and the first bearing flange 10; analogously, a second O-ring 18 can be provided between the second bearing 8 and the second bearing flange 12.

FIG. 2 shows an exemplary embodiment of an electric-motor arrangement having a medium-diverting means. The reference numerals are used analogously. As long as nothing different is stated in the following text, the electric-motor arrangement can be configured in the way shown further above in relation to FIG. 1.

The electric-motor arrangement has a motor housing 2 and a rotor 4 which is arranged in the motor housing 2 so that it can be rotated about an axis L via a bearing 6, the bearing 6 being arranged so that it is gripped in a bearing flange 10; furthermore, the electric-motor arrangement has a stator 14 which is arranged around the rotor 4 in relation to the axis L, and a coupling pin 20 which is arranged around the axis L; furthermore, it has a first medium-line section 30 for guiding a medium, the first medium-line section 30 extending radially outside the rotor in relation to the axis, and a second medium-line section 32 for further guiding the medium, which second medium-line section 32 extends in the coupling pin 20. Here, the second medium-line section 32 is arranged radially closer to the axis L than the first medium-line section 30. Furthermore, the electric-motor arrangement has a medium-diverting means 34 for a connection which guides the medium between the first medium-line section 30 and the second medium-line section 32, this medium-diverting means 34 being formed in the bearing flange 10. As a result of the formation in the bearing flange 10, the seal in the transition regions of first medium-line section 30—medium-diverting means 34, on the one hand, and medium-diverting means 34—second medium-line section 32, on the other hand, can be of lighter and/or improved design.

As is apparent by way of example from FIG. 3, in which the bearing flange 10 is shown in a separated manner, to this end the electric-motor arrangement can have, in particular, a sealing seat 36 for a seal between the medium-diverting means 34 and the second medium-line section 32 and/or a further sealing seat 36' denoted by way of example in FIG. 2 for a seal between the first medium-line section 30 and the medium-diverting means 34. As shown in FIGS. 2 and 3, the sealing seat 36 can be formed in the bearing flange 10. The further sealing seat 36' can be formed in the stator 14. As an alternative, a corresponding sealing seat could also be formed in the coupling pin 20. An O ring 38 and 38' is preferably arranged in the sealing seat 36 and in the further sealing seat 36', respectively.

The bearing flange 10 can correspond to the bearing flange 10 which is called "first bearing flange" further above in relation to FIG. 1. The bearing flange 10 can have a first flat side 103 and a second flat side 104 which are preferably configured parallel to one another. In particular, the first flat side 103 and the second flat side 104 can be configured in each case perpendicularly with respect to the axis L. Here, the medium-diverting means 34 can be formed between the first flat side 103 and the second flat side 104. The first flat side 103 and the second flat side 104 can extend radially to the outside as far as the circumferential face 101 which is called the "first" circumferential face 101 further above in accordance with the context.

Furthermore, the bearing flange 10 can have a projection 105 which, preferably directly from the second flat side 104, extends towards that side which lies opposite the coupling pin 20, the projection 105 extending in the radial direction to a lesser extent than the circumferential face 101 and surrounding the bearing 6 radially; that is to say, in other words, the first bearing 6 is gripped in the region of the projection 105 in the bearing flange 10.

As is shown, furthermore, by way of example in FIG. 2, the first medium-line section 30 can be integrated into the stator 14. As a result, a particularly space-saving, compact design of the electric-motor arrangement is enabled.

As an alternative (not shown in the figures), a flat seal which bears against the bearing flange 10 can be provided for sealing between the first medium-line section 30 and the medium-diverting means 34 or between the medium-diverting means 34 and the second medium-line section 32.

The bearing flange 10 advantageously has a radial hole 40, by which a part of the medium-diverting means 34 is formed. The hole 40 can be provided, in particular, between the first flat face 103 and the second flat face 104. Moreover, a second hole 41 can be provided in the bearing flange 10, which second hole 41 can be configured, in particular, parallel to the axis L and serves for connection between the stator 14 and the radial hole 40, that is to say, as it were, a feed hole for the medium from the stator. Correspondingly, a third hole 42 can be provided which serves for connection between the radial hole 40 and the coupling pin 20. As is apparent from FIG. 3, the sealing seat 36 can be formed directly, for example, by the third hole 42.

Figure 4:
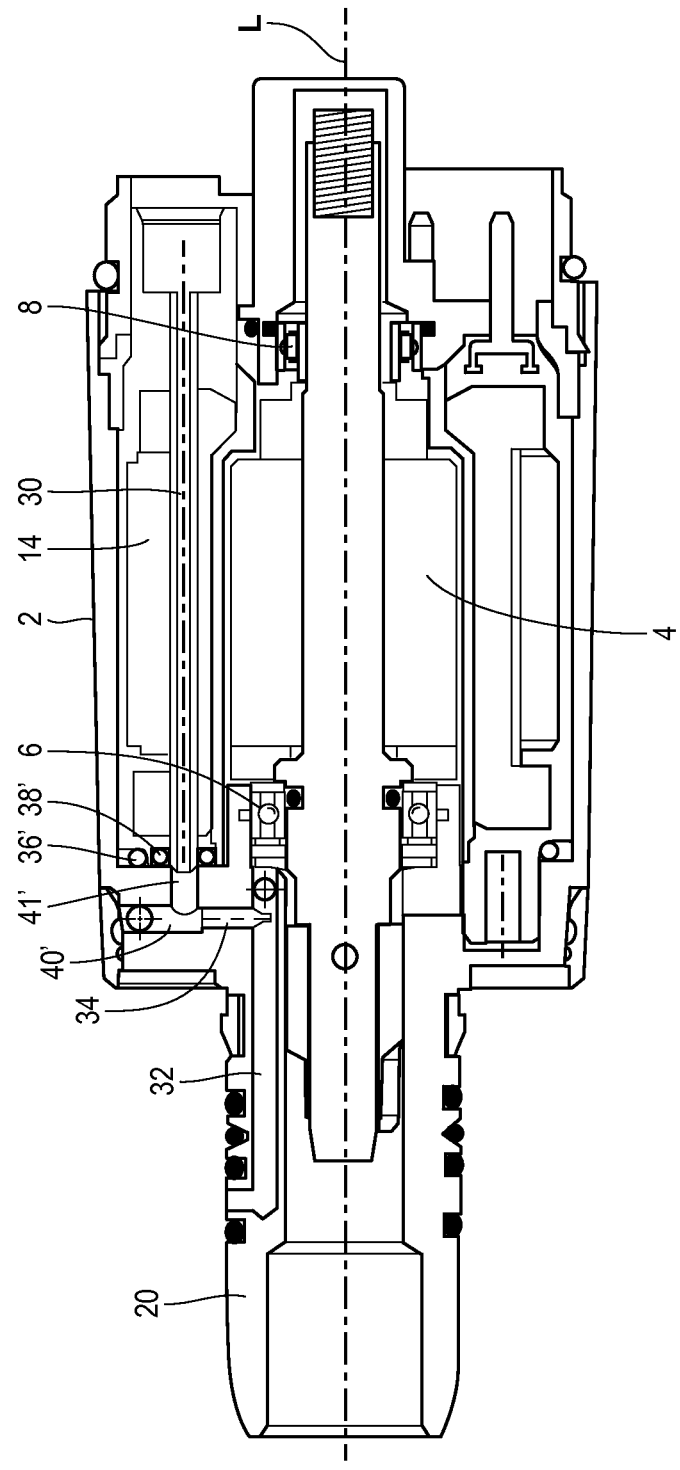
FIG. 4 shows a variation of the electric-motor arrangement shown in FIG. 2, with an integrated bearing flange.

A first variant of the exemplary embodiment of FIG. 2 is shown in FIG. 4, identical elements being provided with the same reference numerals. In this case, the bearing flange is not formed by a separate component, but rather is an integral constituent part of the housing 2. Here too, two holes 40' and 41' are formed in the front region of the housing 2, via which holes 40' and 41' ultimately a connection is achieved between the first medium-line section 30 and the second medium-line section 32. The omission of a separate component which forms the bearing flange leads to a reduction in the connection points to be sealed, which ultimately leads to higher operating reliability, simpler production and a reduction in the production costs.

Figure 5:
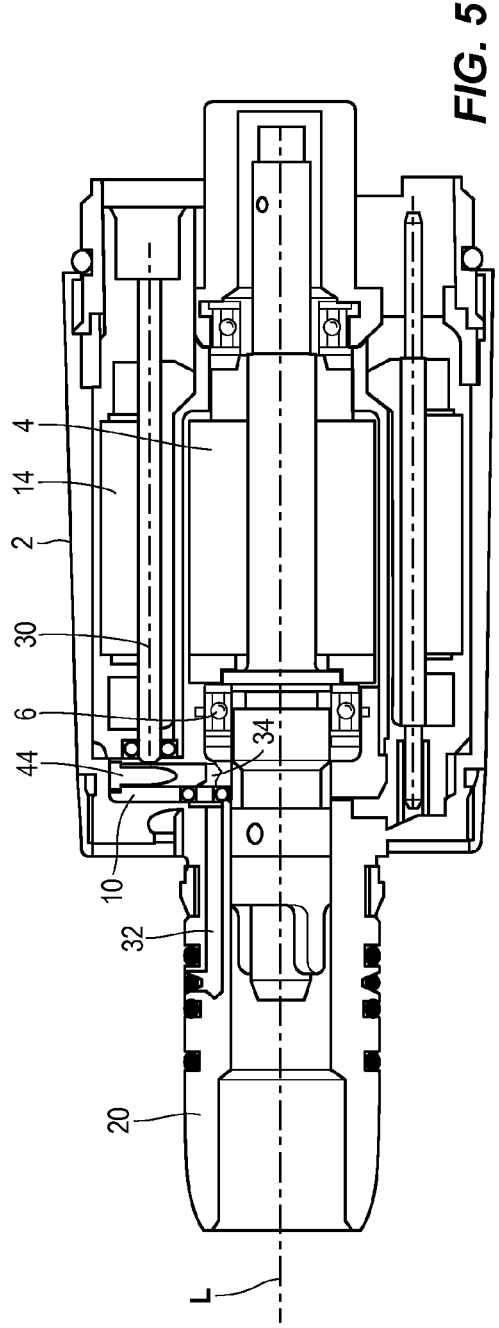
FIG. 5 shows a variation of the electric-motor arrangement shown in FIG. 2, with a suck-back stop.
Figure 6:
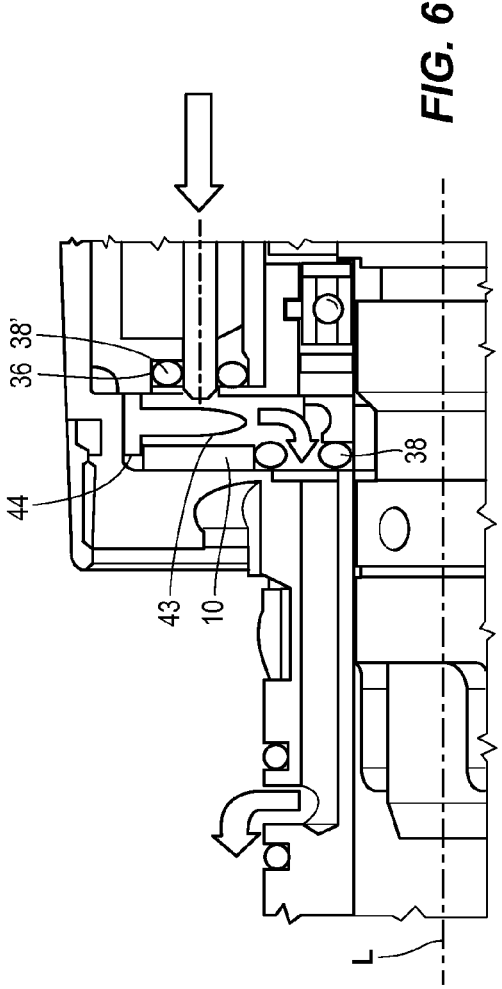
FIG. 6 shows an illustration of a detail from FIG. 5.

FIG. 5 shows a variant, in which a suck-back stop is arranged in the medium-diverting means 34. FIG. 6 shows a detail from FIG. 5. Here, a hose element 43 made from elastic material is arranged in the radial hole 40. The hose element 43 is composed, for example, of rubber, silicone or Viton and is designed so that it bears against an inner wall of the radial hole 40 in such a way that, without the action of external forces, it closes the second hole 41 for the medium from the stator 14 but, in the case of pressure from this inflow side, rises up from the inner wall and the medium flows through in the direction of the handpiece. The medium therefore cannot flow from the coupling pin 20 back to the stator 14 or to the supply hose, with the result that a suck-back stop is thus formed.

Here, furthermore, a pin element 44 is advantageously provided which is arranged in such a way that it protrudes into the hose element 43 and seals the latter radially to the outside with respect to the medium. The pin element 44 is preferably designed in such a way that the hose element 43 is supported by the pin element 44 and can rise up from the inner wall of the radial hole 40 only in a limited way. Moreover, the pin element 44 can close the hole 40 in the radial direction towards the circumference of the bearing flange 10.

As an alternative to the use of the pin element 44, the suck-back stop can also be realized by the use of a lip valve, as is shown in FIGS. 7 and 8. In this case, the hole 41' is configured to be somewhat longer and with a larger diameter, in order to make it possible to receive the lip valve 44'. Here, the bearing flange can once again be an integral constituent part of the housing 2, as is shown in FIGS. 7 and 8, or can also be formed by a separate element, analogously to the variant according to FIG. 3. Furthermore, it would also be conceivable to arrange the lip valve 44' in the radial hole 40'.

Figure 9:
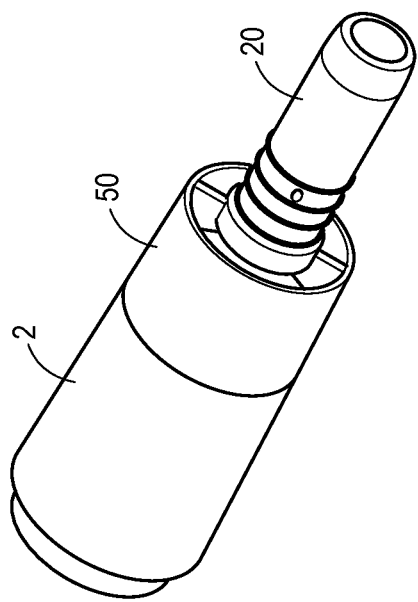
FIG. 9 shows a perspective view of a dental instrument part.
Figure 10:
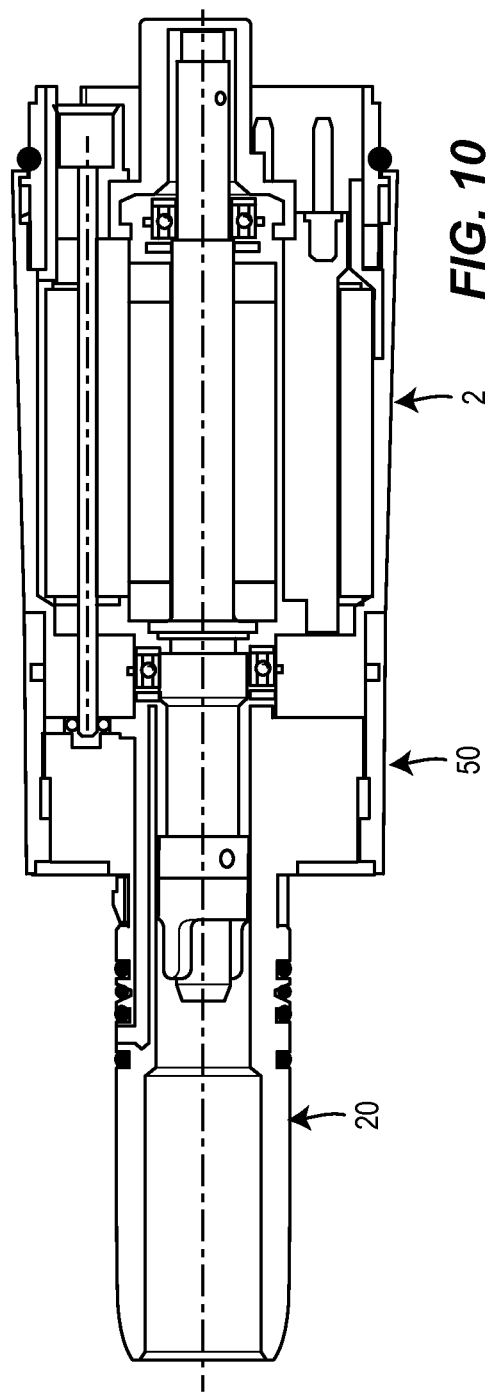
FIG. 10 shows an associated longitudinal section.

FIGS. 9 and 10 show a perspective view of a dental-instrument part, FIG. 10 showing an associated longitudinal section. As is shown by way of example in the two figures, the dental instrument part can be an electric-motor arrangement. The dental instrument part has an outer surface which is composed of titanium; the surface is tempered by a hardening process. In particular, the surface can be tempered in a manner based on a thermo chemical diffusion process.

Gas nitriding, laser gas nitriding, gas carbonitriding, boronizing and oxidizing belong to the thermo chemical diffusion processes for titanium. The thermo chemical diffusion process is preferably what is known as "oxygen diffusion hardening" (ODH). Since these layers are formed from the basic material, they do not tend to flake off, in contrast to PVD layers. No foreign-material coating materials are used. The layer thicknesses can be controlled, to be precise via process parameters such as residence time, temperature and pressure. The tempered surface is particularly satisfactorily biocompatible.

For special tribological requirements, the surface layer which is produced by means of thermochemical diffusion processes can be used as supporting structure for a DLC ("diamond-like carbon") hard material coating (PVD process) or a pure CVD diamond coating.

The dental instrument part preferably has a coupling pin 20 which is provided for connection to a further dental instrument part, for example to a hand piece and angular piece, the outer surface being an outer surface of the coupling pin 20. The loading on the coupling pin 20 as a result of attachment and pulling off of the hand piece is particularly great. It can be provided that only the coupling pin 20 is tempered, but it can also be provided that the motor housing 2 is also correspondingly tempered.

The layer thickness produced by the ODH tempering can be, for example, between 5 and 25 micrometers. The surface hardness which is achieved can lie, for example, between 500 and 1000 HV.

If the thermo chemical diffusion process is boronzing, the layer thickness which is produced by the tempering can be, for example, between 2 and 25 micrometers and the surface hardness achieved can be, for example, between 2000 and 4000 HV.

If the thermo chemical diffusion process is nitriding, the layer thickness which is produced by the tempering can be, for example, between 2 and 10 micrometers and the surface hardness which is achieved can be, for example, more than 800 HV.

In the example shown in FIGS. 9 and 10, the electric-motor arrangement furthermore has a sleeve 50. In order to reduce weight, the components coupling pin 20 and coupling, sleeve 50 and motor housing 2 can be produced from titanium. In order to avoid "scoring", the surface of the coupling pin 20 is tempered as described. In order to achieve a scratch-resistant surface, the sleeve 50 and/or the motor housing 2 can also be tempered from titanium.

Figure 11:
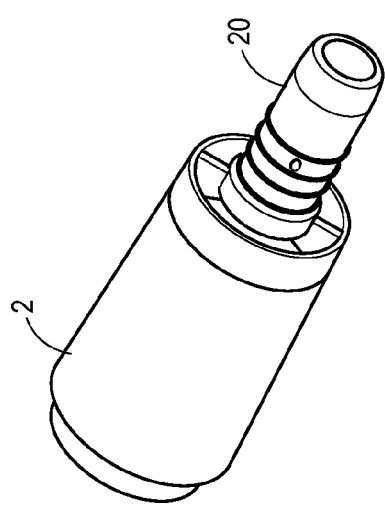
FIG. 11 shows a perspective view of a further dental instrument part.
Figure 12:
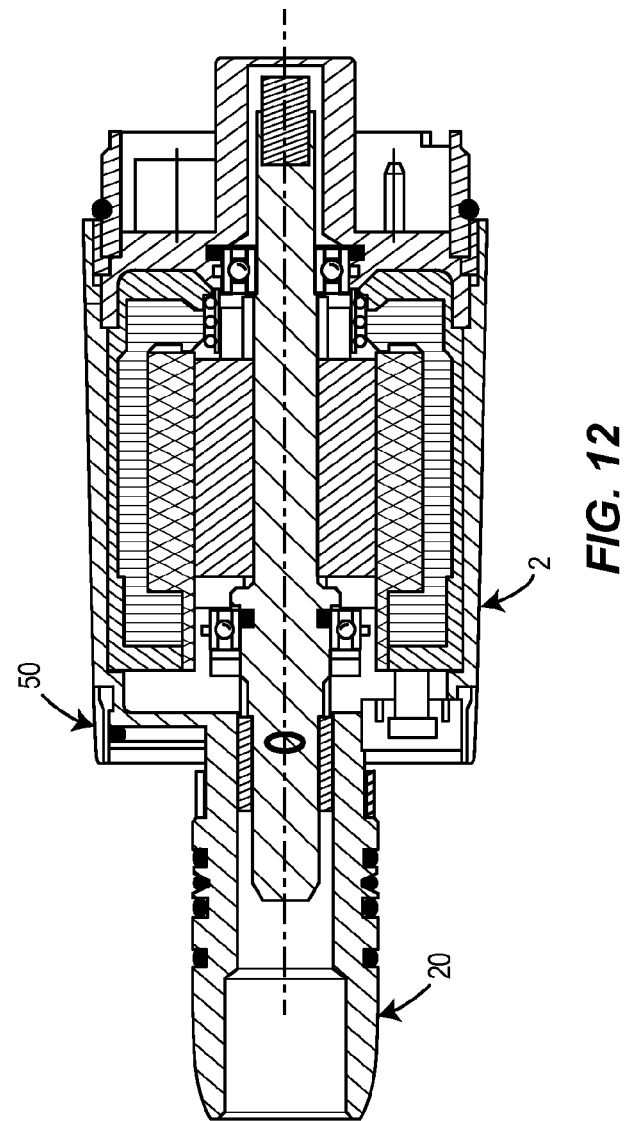
FIG. 12 shows an associated longitudinal section.

FIGS. 11 and 12 show a further example, in which the motor housing 2 and the coupling pin 20 have a tempered titanium surface as described. Here, the motor housing 2 and the coupling pin 20 are configured in one piece or integrally.

Figure 13:
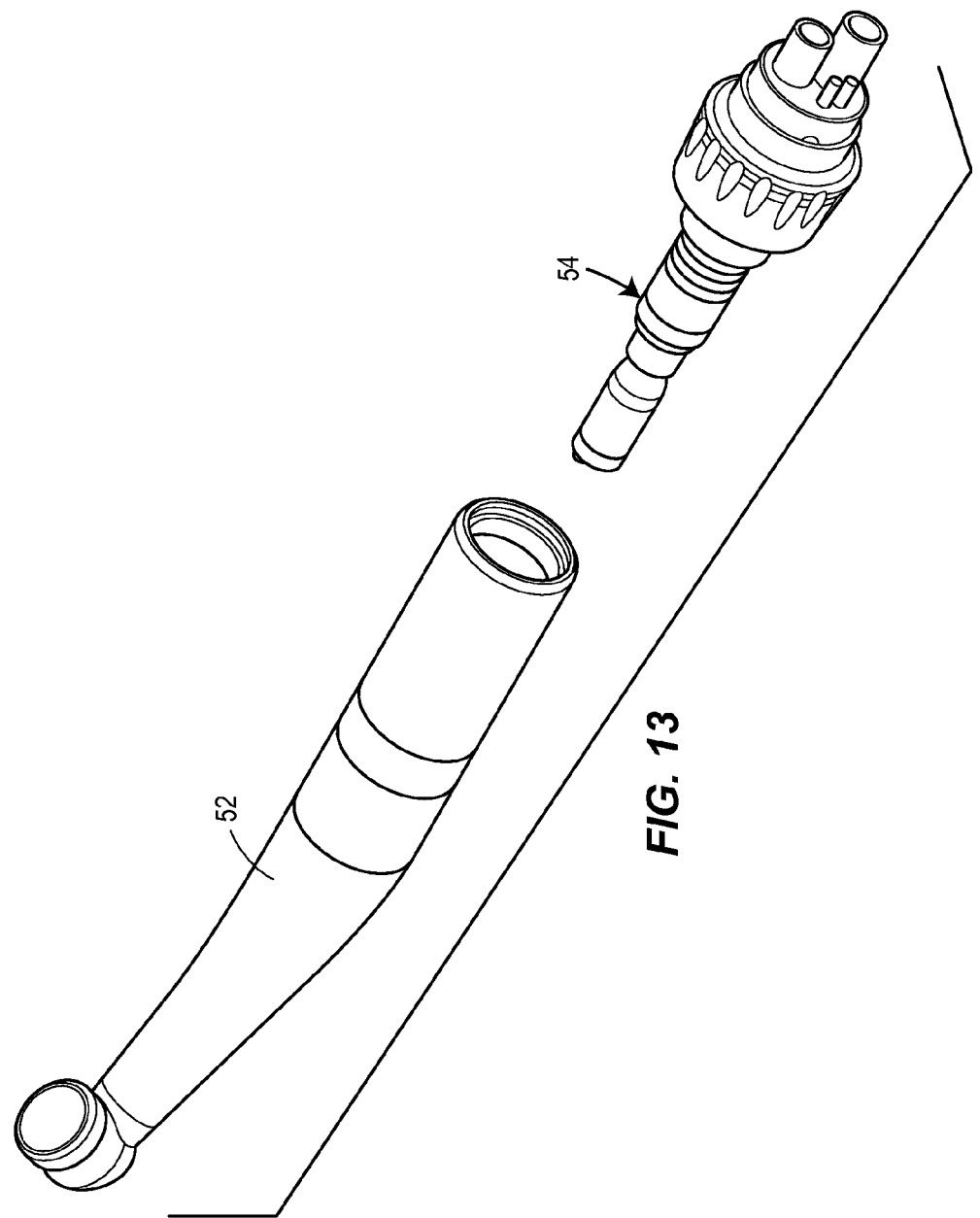
FIG. 13 shows a perspective view of a turbine with a MULTIflex coupling.
Figure 14:
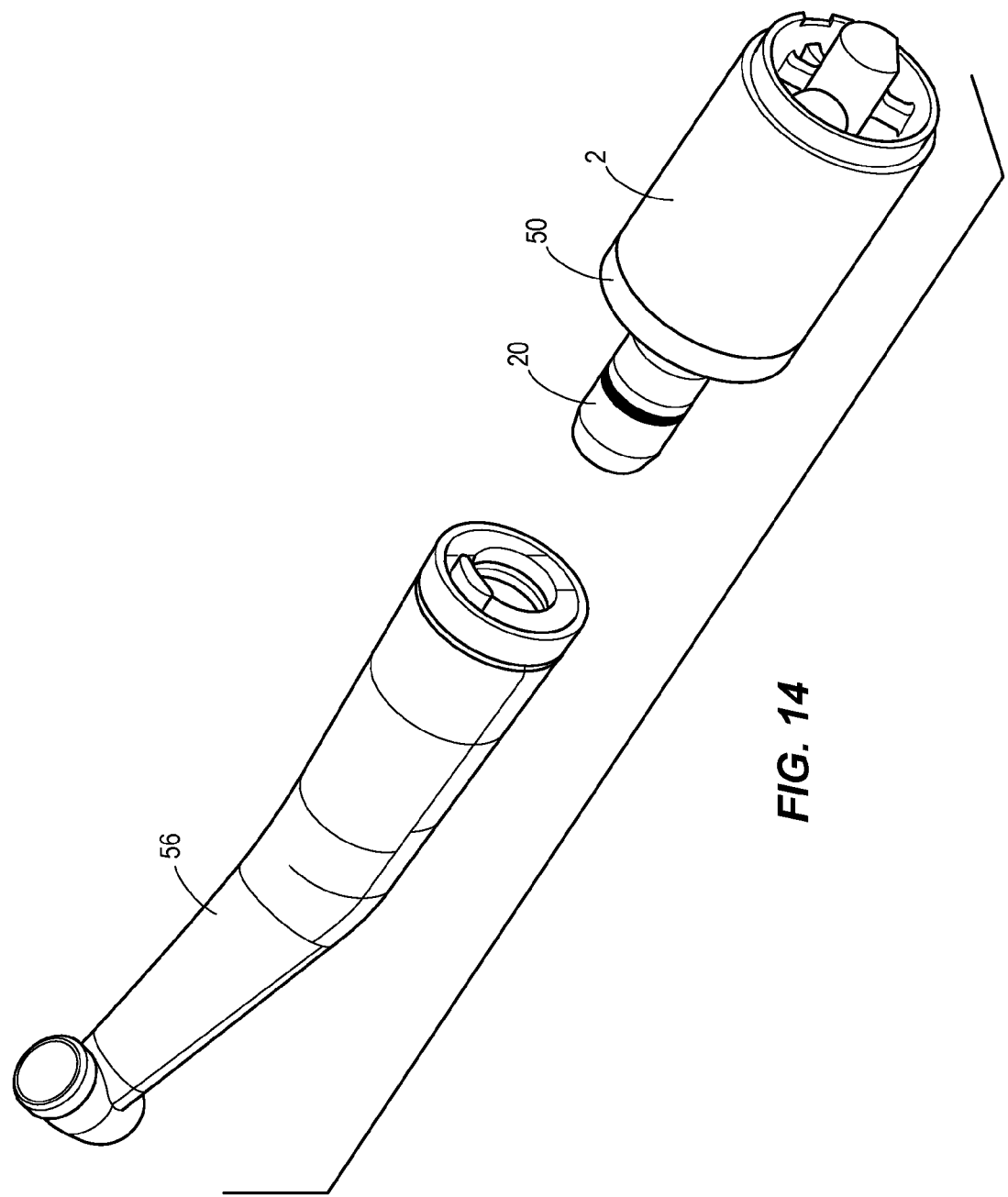
FIG. 14 shows a perspective view of a hand piece and angular piece with an associated electric-motor arrangement.

FIG. 13 outlines a turbine with a MULTIflex coupling, in which the turbine housing 52 and the coupling pin 54 of the MULTIflex coupling are tempered from titanium. FIG. 14 outlines a hand piece and angular piece 56 with an associated electric-motor arrangement; the hand piece and the angular piece 56, the coupling pin 20, the sleeve 20 and the motor housing 2 can be tempered from titanium.

Figure 15:
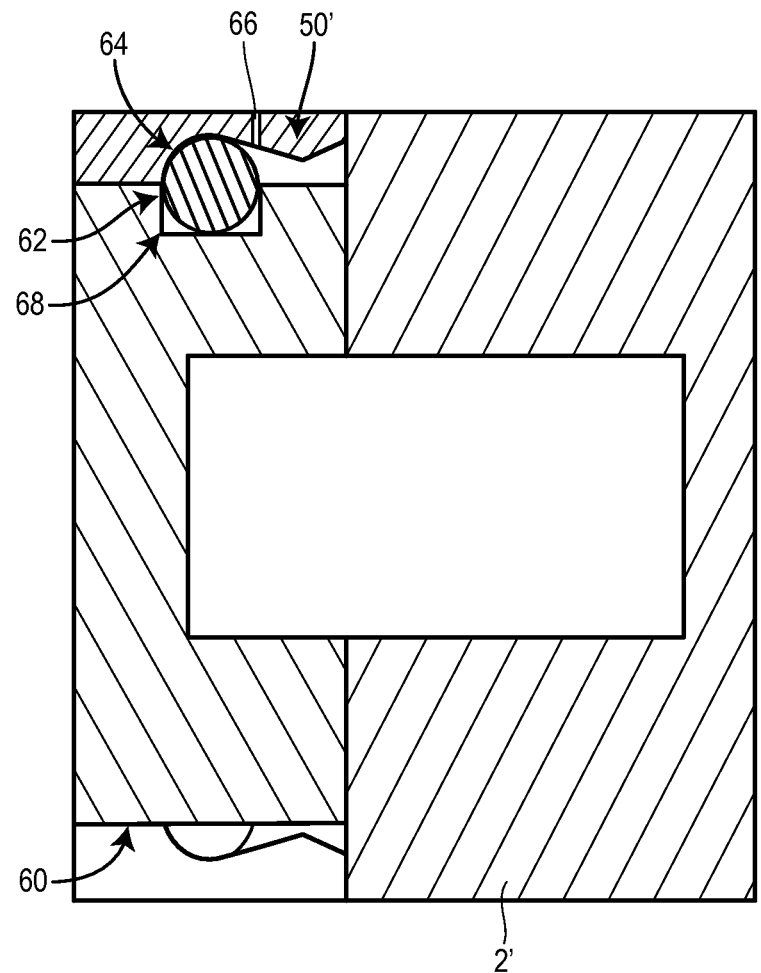
FIG. 15 shows an outline sketch of a dental instrument with a holding mechanism for an instrument part.

FIG. 15 shows an outline which shows the principle of a holding mechanism according to the invention for a dental instrument. The dental instrument has a housing 2' which can be, for example, the motor housing 2 shown further above of an electric-motor arrangement according to the invention. Furthermore, the dental instrument has an instrument part 50' which is arranged removably on the housing 2'. The instrument part 50' can be, for example, the sleeve 50 shown further above. The instrument part 50' has an annular region which is arranged so as to reach around an outer circumferential face 60 of the housing 2'; for example, the annular region can extend around the abovementioned axis L.

A depression 62, for example a blind hole or a groove, is arranged on the outer circumferential face 60, in which depression 62 at least one preferably spherical, elastic holding part 64 is received. The elastic holding part can be, for example, an elastic rubber part; for example, rubber balls, for example made from FKM, can therefore be provided as holding parts 64. An undercut 66 is arranged in the annular region of the instrument part 50', into which undercut 66 the at least one elastic holding part 64 engages. The depression 62 is advantageously configured in such a way that the elastic holding part 64 only partially fills the volume which is defined by the depression 62.

A plurality of, for example three, correspondingly configured spherical holding parts 64 can advantageously be provided which are preferably arranged uniformly over the circumference, that is to say, for example, offset in each case by 120° in the case of three holding parts 64. Here, in each case one blind hole can be provided for each of the holding parts 64. In the case of a groove, the groove can extend over the entire circumference. A hollow or also a plurality of hollows can also be provided correspondingly.

Inclined slopes are preferably made in the instrument part 50', which inclined slopes merge into the preferably rounded undercut 66 or the back taper. During attachment of the instrument part 50' or the sleeve, the holding parts 64 are deformed by the inclined slopes and subsequently latch in the undercut 66. In particular, no radially acting helical springs are required.

During release, the holding parts 64 are deformed again under the pull-off pressure and the instrument part 50' can be pulled off again.

The longitudinal-section shape of the undercut 66, as is apparent from FIG. 15, is preferably adapted to the shape of the holding part 64. Here, the design is advantageously such that the spherical holding parts 64 are unloaded when the instrument part 50' is connected as provided to the housing 2'. In this unloaded state, each of the holding parts 64 has its greatest volume. This volume is also available for a deformation of the holding parts 64 during the pulling off and attaching of the instrument part 50'. The holding parts 64 are preferably seated in depressions 62 in the form of blind holes and seal the latter at the circumferential line against penetrating liquids and contaminants. In relation to FIG. 15, "below", in general that is to say radially within, this circumferential line or circumferential face, each of the blind holes 62 is designed in such a way that the relevant holding part 64 can lie on a flat rest or supporting face, a clearance being formed between the circumferential line and the rest or supporting face, which clearance is available for a deformation of the holding part 64 during the pulling off and attaching of the instrument part 50', that is to say a "deformation space" 68, as it were.

In comparison with a snap-in connection with an O-ring, the holding mechanism can be designed in such a way that the mating forces which are required for pulling off and attaching are lower. The tolerance requirements are lower. Larger undercuts can also be realized, which contributes to the functional reliability.

If the instrument part 50' is rotated during the attaching or pulling off, the required forces are reduced further, since in the process the spherical holding parts 64 move to or make contact with the inclined slope on a line of lesser gradient.

Figure 16:
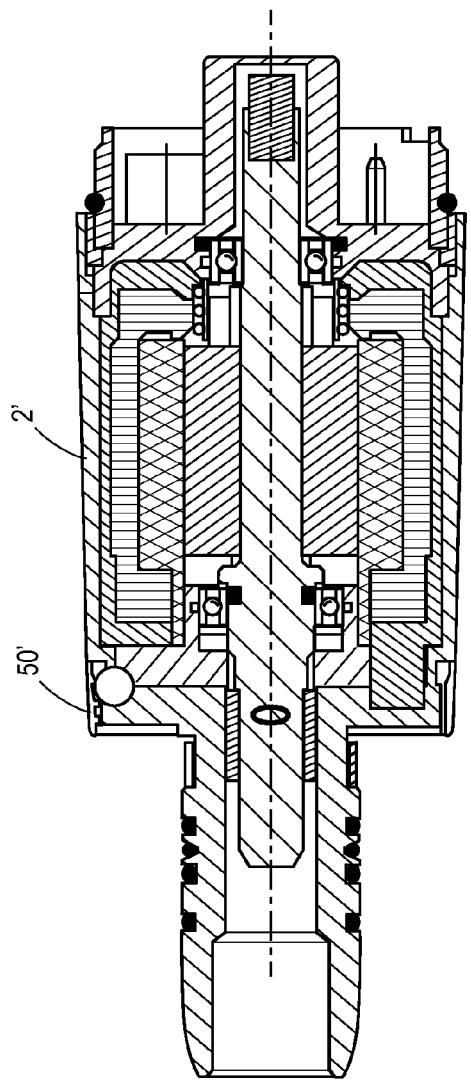
FIG. 16 shows a longitudinal section through an electric-motor arrangement with a holding mechanism according to the invention for a sleeve.
Figure 17:
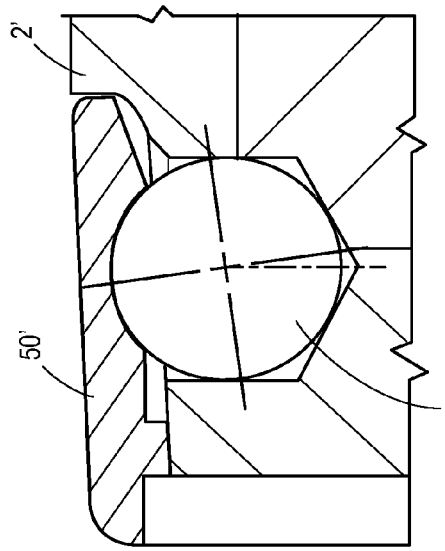
FIG. 17 shows a detail from FIG. 16.

FIG. 16 shows a longitudinal section through a corresponding electric-motor arrangement with a sleeve 50' which is arranged and held on the housing 2' via a holding mechanism or snap-in connection according to the invention. FIG. 17 shows on an enlarged scale how the ball 64 latches in a groove of the sleeve 50'.

Figure 18:
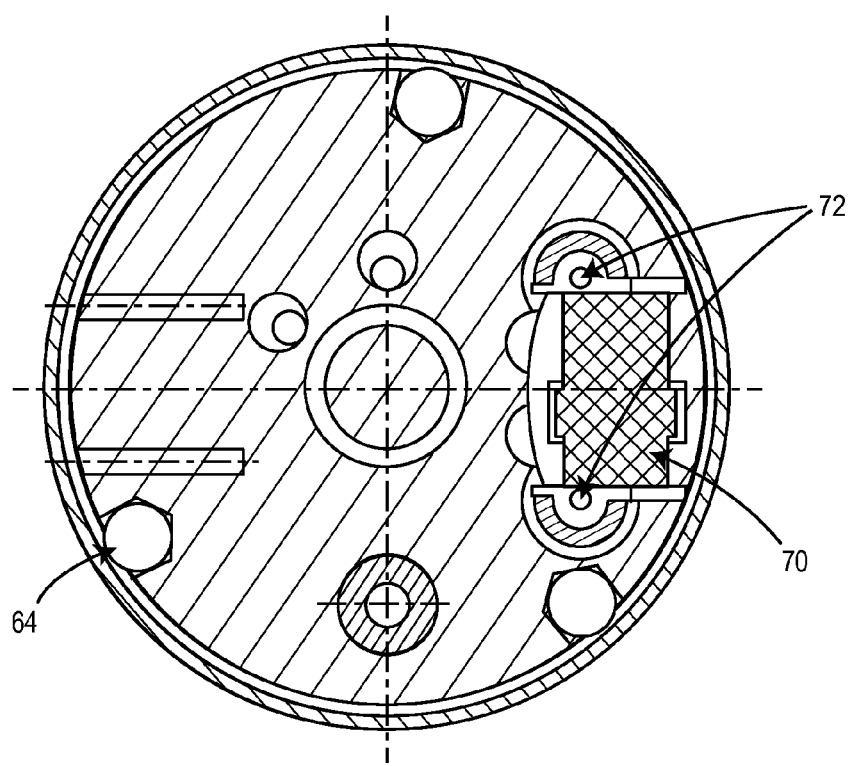
FIG. 18 shows a cross section through a holding mechanism according to the invention.

FIG. 18 shows a cross section, in which it is seen how three holding parts 64 are arranged in the form of rubber balls distributed uniformly over the circumference, that is to say in each case at a 120° spacing. The reference numeral 70 denotes an LED board, and the reference numeral 72 denotes a contact of an LED module.

The invention claimed is:

1. Electric-motor arrangement for a medical handpiece, comprising:
   a motor housing attachable to and detachable from a handpiece body,
   a rotor arranged in the motor housing so that it can be rotated about an axis via a first bearing and a second bearing,
   a stator arranged around the rotor in relation to the axis,
   a first bearing flange in which the first bearing is received, and
   a second bearing flange, in which the second bearing is received,
   wherein the first bearing flange comprises metal and has a first circumferential face directly adjoining the motor housing, and the second bearing flange comprises metal and has a second circumferential face directly adjoining the motor housing, and
   the stator is clamped between the first and second bearing flanges.

2. Electric-motor arrangement according to claim 1, wherein the stator is centered radially in the motor housing in relation to the axis by the first and second bearing flanges.

3. Electric-motor arrangement according to claim 1, further comprising a coupling element for connecting the electric-motor arrangement to the medical handpiece.

4. Electric-motor arrangement according to claim 3, wherein the coupling element is a coupling pin.

5. Electric-motor arrangement according to claim 3, wherein the coupling element is configured in one piece with the motor housing.

6. Electric-motor arrangement according to claim 1, wherein the medical handpiece is a dental handpiece.

7. Electric-motor arrangement according to claim 1, the first bearing flange including a first flat side and a second flat side that is parallel to the first flat side, the first flat side and the second flat side being perpendicular to the axis.

8. Electric-motor arrangement according to claim 7, the first flat side and the second flat side extending radially outwardly to the first circumferential face.

9. Electric-motor arrangement according to claim 8, the first bearing flange including a projection, which extends from the second flat side, opposite a coupling element.

10. Electric-motor arrangement according to claim 9, the projection extending in a radial direction a lesser distance than the first circumferential face.

11. Electric-motor arrangement according to claim 10, wherein the first bearing is gripped in the region of the projection.

12. Electric-motor arrangement according to claim 3, the rotor including a rotor axle and the coupling element surrounds the rotor axle and the coupling element extends longitudinally beyond a first end of the rotor axle, the coupling element extending parallel to the axis.

* * * * *